United States Patent [19]

Yamamoto et al.

[11] Patent Number: 5,422,343
[45] Date of Patent: Jun. 6, 1995

[54] PROPHYLACTIC AND THERAPEUTIC COMPOSITION FOR MRSA INFECTION

[75] Inventors: Sigeru Yamamoto, Naha; Hiroomi Yokoyama, Naruto, both of Japan

[73] Assignee: Otsuka Pharmaceutical Factory, Inc., Naruto, Japan

[21] Appl. No.: 26,744

[22] Filed: Mar. 5, 1993

[30] Foreign Application Priority Data

Dec. 21, 1992 [JP] Japan .................................. 4-340523

[51] Int. Cl.⁶ .............................................. A61K 31/70
[52] U.S. Cl. ........................................ 514/45; 514/46; 514/47; 514/48; 514/49; 514/50; 514/51
[58] Field of Search ................ 514/47, 48, 49, 50, 514/51, 45, 46; 536/26.74, 26.8, 26.7, 27.8, 27.81, 28.4, 28.54, 28.53

[56] References Cited

U.S. PATENT DOCUMENTS

| | | | |
|---|---|---|---|
| 4,758,553 | 7/1988 | Ogoshi | 514/47 |
| 5,231,085 | 7/1993 | Alexander et al. | 514/44 |
| 5,246,708 | 9/1993 | von Borstel et al. | 424/450 |
| 5,268,365 | 12/1993 | Rudolph et al. | 514/44 |
| 5,320,846 | 6/1994 | Bistrian et al. | 424/439 |

OTHER PUBLICATIONS

J. Nutr. Sci. Vitaminol., 38, 22–225 (1992).
CA vol. 103, No. 24, 200878z.
CA vol. 113, No. 24, 217811b.

*Primary Examiner*—Douglas W. Robinson
*Assistant Examiner*—Anita Varma
*Attorney, Agent, or Firm*—Armstrong, Westerman, Hattori, McLeland and Naughton

[57] ABSTRACT

The invention provides an anti-MRSA prophylactic-/therapeutic composition containing as an active ingredient at least one nucleic acid component selected from among inosine, guanosine n'-monophosphate (GMP) (n'=2', 3'or 5'), uridine and thymidine.

6 Claims, No Drawings

PROPHYLACTIC AND THERAPEUTIC COMPOSITION FOR MRSA INFECTION

TECHNICAL FIELD

The present invention relates to the prophylaxis and therapy of MRSA infection and more particularly to a novel prophylactic and therapeutic composition comprising at least one nucleic acid component selected from a defined group of nucleic acid bases, nucleosides and nucleotides as an active ingredient.

PRIOR ART AND PROBLEMS THEREOF

MRSA is an acronym of methicillin-resistant *Staphylococcus aureus* which is known to produce a variety of toxins and enzymes such as enterotoxin, coagulase and so forth. As such, MRSA is a major pathogenic microorganism causative of hospital infections which affect a broad range of organs including the skin, gastrointestinal tract, respiratory tract and urinary tract. Unlike the exogeneous microorganisms such as *Pseudomonas spp.* which have for years been blamed for hospital infections, *Staphylococcus aureus* is a member of the resident bacterial flora in man and the high frequency of MRSA carriers among patients and hospital employees makes it difficult to control MRSA infections within hospitals. Moreover, since MRSA is highly resistant to many antibacterial agents and its infection usually follows a refractory course, it is presenting a serious clinical problem. The therapeutic drugs which can be indicated in MRSA infection are no more than a few at the present, that is say only vancomycin, minomycin, fosfomycin, cefamethase and cefuzonam can be reckoned, and, moreover, it is very likely that even these drugs will also encounter the resistance problem soon. Therefore, the development of a new alternative prophylactic/therapeutic drug effective against MRSA infection has been earnestly awaited.

The object of the present invention, therefore, is to provide a novel and effective drug for the prevention and therapy of MRSA infection.

The inventors of the present invention previously discovered that certain compositions of nucleic acid components, intravenously administered particularly in the form of a hyperalimentation fluid, promote protein synthesis and assist in nutritional control and maintenance of nitrogen balance (Japanese Patent Application Kokai 60-126220). Subsequent research led them to a surprising discovery that some of said nucleic acid component compositions are effective in the prevention and therapy of MRSA infection. The inventors further discovered that the prophylactic/therapeutic effects of such compositions can be potentiated by using a certain amino acid, namely arginine and/or glutamine, in combination. The present invention has been conceived and developed on the basis of the above findings.

DISCLOSURE OF THE INVENTION

There is, thus, provided by the invention a prophylactic/therapeutic composition for MRSA infection which comprises as an active ingredient at least one nucleic acid component selected from the group consisting of inosine, guanosine n'-monophosphate (n'=2', 3' or 5'), uridine and thymidine.

The anti-MRSA prophylactic/therapeutic composition of the invention may comprise at least one nucleic acid component selected from the above-mentioned group consisting of inosine, guanosine n'-monophosphate (GMP), uridine and thymidine as an essential active ingredient and, in combination therewith, at least one nucleic acid component selected from the group consisting of nucleic acid bases, nucleosides and nucleotides as an optional ingredient. The ingredients to be used optionally in such a combination may not be different from those constituting the compositions of nucleic acid components as disclosed in the previous application referred to above. Thus, as the nucleic acid bases, there can be employed adenine, hypoxanthine, guanine, cytosine, uracil, thymine, orotic acid, etc. and nontoxic salts (e.g. sodium salts) thereof. As said nucleosides, there can be employed adenosine, inosine, guanosine, cytidine, uridine, orotidine, etc. and, further, deoxyribonucleosides such as deoxyadenosine, deoxyguanosine, deoxycytidine, deoxyuridine, thymidine etc., inclusive of their nontoxic salts. As said nucleotides, mono- to triphosphates of said nucleosides and their nontoxic salts can be mentioned. The following is a partial listing of such nucleotides.

Ribonucleotides: adenosine n'-monophosphate (AMP), adenosine n'-diphosphate (ADP), adenosine n'-triphosphate (ATP), inosine n'-monophosphate (IMP), inosine n'-diphosphate (IDP), inosine n'-triphosphate (ITP), guanosine n'-monophosphate (GMP), guanosine n'-diphosphate (GDP), guanosine n'-triphosphate (GTP), cytidine n'-monophosphate (CMP), cytidine n'-diphosphate (CDP), cytidine n'-triphosphate (CTP), uridine n'-monophosphate (UMP), uridine n'-diphosphate (UDP), uridine n'-triphosphate (UTP), etc. (where n' means 2', 3' or 5')

Deoxyribonucleotides: deoxyadenosine n'-monophosphate (dAMP), deoxyadenosine n'-diphosphate (dADP), deoxyadenosine n'-triphosphate (dATP), deoxyguanosine n'-monophosphate (dGMP), deoxyguanosine n'-diphosphate (dGDP), deoxyguanosine n'-triphosphate (dGTP), deoxycytidine n'-monophosphate (dCMP), deoxycytidine n'-diphosphate (dCDP), deoxycytidine n'-triphosphate (dCTP), thymidine n'-monophosphate (TMP), thymidine n'-diphosphate (TDP), thymidine n'-triphosphate (TTP), etc. (where n' means 2', 3' or 5').

It should be understood that, throughout this specification, the above nucleotides will be designated by the abbreviations, shown in parentheses, which are in accordance with the rules of nomenclature of IUPAC-IUB and the common usage the field of peptide chemistry.

The anti-MRSA prophylactic/therapeutic composition of the invention preferably comprises as an active ingredient at least one nucleic acid component selected from the group consisting of inosine, GMP, uridine and thymidine and, in combination therewith, one or more nucleic acid components (nucleic acid bases, nucleosides and nucleotides) mentioned above by way of example. Particularly preferred combinations of active ingredients are the following 5-member combinations. cytosine/thymidine/GMP/UMP/IMP, thymine/inosine/AMP/CMP/GMP, AMP/CMP/GMP/UMP/TMP, AMP/CMP/dGMP/UTP/IMP, cytosine/uridine/AMP/CMP/UMP, adenine/cytosine/inosine/UMP/TDP, thymine/CMP/dATP/dGMP/UTP, thymidine/AMP/CMP/GMP/UMP, thymidine/CMP/GMP/UMP/IMP, cytosine/thymidine/GMP/UMP/IMP and inosine/cytidine/GMP/uridine/thymidine.

The preferred species and proportions of the above 5-member combinations are as follows.

Inosine:cytidine:GMP:uridine:thymidine=4:4:4:3:1 (mol ratio, the same applies hereinafter) and 4:0.04:4:3:1; AMP:CMP:GMP:UMP:thymidine=4:4:4:3:1; and CMP:GMP:UMP:IMP:thymidine=4:4:3:4:1 and 2:2:1:2:1.

It is known that AMP is metabolized to IMP in the body and, therefore, AMP and IMP can be partially or wholly substituted by each other.

The combination of active ingredients in the present invention is not limited to the above 5-member combinations but such basal combinations may be supplemented with one or more other nucleic acid components to provide 6- or more multi-member compositions. Among preferred combinations of 6 ingredients, for instance, are: cytosine/inosine/AMP/UMP/GMP/IMP, adenine/inosine/thymidine/CMP/UMP/IMP, dAMP/ATP/GMP/UDP/IMP/dCMP, guanosine/inosine/uridine/UMP/IMP/dGMP, AMP/CMP/dGMP/UTP/TMP/IMP, thymidine/CMP/GMP/UMP/IMP/TMP, cytosine/thymidine/UMP/CMP/dAMP/dGMP, ATP/dCMP/GMP/UDP/TTP/IMP and so on.

The anti-MRSA composition of the invention may further comprise, in addition to the above nucleic acid components, at least one amino acid selected from the group consisting of arginine and glutamine. The use of such amino acid in combination with said nucleic acid components results in a further potentiation of the anti-MRSA prophylactic/therapeutic effect of said combination of nucleic acid components. The amino acid can be incorporated, in a suitable proportion, in a composition comprising said nucleic acid component or components for administration in a single dosage form or can be formulated into an independent dosage form for administration in combination with a separate dosage form comprising said composition of nucleic acid component or components. In either case, the proportion of said amino acid relative to said active ingredient nucleic acid component or components is generally about 1 to 100 parts by weight and preferably about 2 to 30 parts by weight.

To manufacture the Anti-MRSA composition of the present invention, the active ingredient nucleic acid component or components, optionally with or without said amino acid, may be simply blended. Generally, however, the composition is formulated and processed into a suitable unit dosage form according to the intended route and method of administration. As examples of said unit dosage form, there can be mentioned a variety of liquid dosage forms such as injections for intravenous administration or a variety of semisolid or solid dosage forms suitable for oral, parenteral or local administration, such as powders, tablets, pills, granules, fine granules, solutions, suspensions, emulsions, capsules, suppositories, syrups, ointments and so on. Such unit dosage forms can be manufactured using suitable pharmaceutical carriers, optionally with or without the use of additives, in the per se conventional manner. Among the additives mentioned above are diluents, excipients, etc. used commonly according to respective dosage forms, such as fillers, volume builders, binders, humectants, disintegrators, surfactants, lubricants and so on.

The amino acid for use as a potentiator can also be processed optionally into suitable dosage forms similar to those mentioned above.

To be more specific, tablets can be manufactured using a suitable excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose solution, starch solution, gelatin solution, carboxymethylcellulose, hydroxypropylcellulose, methylcellulose, polyvinylpyrrolidone, etc., disintegrators such as sodium carboxymethylcellulose, calcium carboxymethylcellulose, low-substituted hydroxypropylcellulose, dried starch, sodium alginate, agar powder, laminaran powder, sodium bicarbonate, calcium carbonate, etc., a surfactant such as polyoxyethylene sorbitan fatty acid esters, sodium lauryl sulfate, stearyl monoglyceride, etc., a disintegration inhibitor such as sucrose, stearin, cacao butter, hydrogenated oil, etc., absorption accelerators such as quaternary ammonium base, sodium lauryl sulfate, etc., a humectant such as glycerin, starch, etc., an adsorbent such as starch, lactose, kaolin, bentonite, colloidal silica, etc. and a lubricant such as purified talc, stearic acid salts, boric acid powder, polyethylene glycol and so on. Such tablets can be coated in the per se conventional manner to provide dragees, gelatin-coated tablets, enteric-coated tablets, film-coated tablets, etc. or further processed into double-layer or multi-layer tablets.

Carriers useful for shaping the preparation into pills are glucose, lactose, starch, cacao butter, hydrogenated vegetable oils, kaolin, talc and like excipients; gum arabic powder, tragacanth gum powder, gelatin, ethanol, and like binders; laminaran, agar powder and like disintegrating agents, for instance.

Carriers for shaping the preparation into suppositories are polyethylene glycol, cacao butter, higher alcohols, esters of higher alcohols, gelatin, semisynthetic glyceride and the like.

Capsules are usually manufactured by the conventional method, for example by mixing the active component or components of the invention with the carriers as exemplified above, and encapsulating the mixture into hard-gelatin capsules, soft-gelatin capsules or the like.

Injectable solutions, emulsions and suspensions are sterilized and preferably made isotonic to the blood. Diluents useful for the manufacture of such injections include water, ethanol, polyethylene glycol, propylene glycol, ethoxylated isostearyl alcohol, polyoxylated isostearyl alcohol, polyoxyethylene sorbitan fatty acid esters and the like. In preparing isotonic solutions, sodium chloride, glucose or glycerin may be added in an amount sufficient to make the solution isotonic. The anti-MRSA composition of the invention may further contain solubilizers, buffers, local anesthetics, etc. which are commonly employed.

When the composition of the invention is to be provided in the form of an ointment, such as a paste, cream or gel, there can be employed a variety of bases such as white petrolatum, paraffin, glycerin, cellulose derivatives, polyethylene glycol, silicone, bentonite and so on.

The anti-MRSA composition of the invention may further contain a suitable colorant, preservative, perfume, flavorant, corrigent, sweetener, etc. as well as other pharmacologically active substances as required.

The anti-MRSA composition of the invention can be provided in the form of an infusion, too. Such an infusion may contain carbohydrates, such as glucose, fructose, xylitol, sorbitol, maltose, etc., lipids, vitamins, electrolytes, trace elements and so on. If necessary, a suitable stabilizer, pH control agent and/or other additives can also be incorporated.

There is virtually no limitation on the proportion of the active ingredient in the composition of the invention. Although the proportion can be selected from a broad range, it is preferably about 0.5 to 10 weight % based on the final preparation.

Particularly, the infusion according to the invention is provided in the pH range of 3.0 to 8.0, preferably 5.0 to 7.5, and the concentration of all active ingredients therein can be about 0.5 to 10 w/v% and preferably 2 to 8 w/v%.

The methods of administration of the various preparations described above can be liberally selected according to the dosage form, patient's age, sex and other characteristics, severity of disease and other factors. For example, tablets, pills, solutions, suspensions, emulsions, granules, capsules, etc. are orally administered, while injectable preparations can be injected intravenously as they are or after blending with an ordinary glucose, amino acid or other infusion. If necessary, injectable preparations may be administered intramuscularly, intradermally, subcutaneously or intraperitoneally. Suppositories are administered rectally.

The dosage of the anti-MRSA composition of the invention can be liberally selected according to the route of administration, the patient's age, sex and other background factors, severity of condition and so on. Generally, however, the daily dosage as the active ingredient is about 5 to 12 mg per kg body weight. The composition can be administered in 1 to 4 divided doses.

The composition of the invention in the form of an infusion can be administered at the rate of about 10 to 250 ml per day per adult human and preferably about 20 to 100 ml on the same basis.

Thus, the anti-MRSA prophylactic/therapeutic composition of the present invention employs active ingredients which have never heretofore proposed or envisaged and yet provides excellent prophylactic and therapeutic efficacy in MRSA infections.

The following formulation and pharmacologic test examples for the prophylactic and therapeutic composition of the invention are intended to describe the invention in further detail and demonstrate the usefulness of the composition.

EXAMPLE 1

TABLE 1

| Nucleic acid component | w/v % | mMol/l | Mol ratio |
| --- | --- | --- | --- |
| 5'-AMP-2Na | 2.34 | 59.8 | 4 |
| 5'-CMP-2Na | 2.20 | 59.9 | 4 |
| 5'-GMP-2Na | 2.44 | 59.9 | 4 |
| 5'-UMP-2Na | 1.65 | 44.8 | 3 |
| Thymidine | 0.36 | 14.9 | 1 |
| Total free nucleic acid components | | 8 w/v % | |

Pure crystals of the above nucleic acid components, in the proportions giving the indicated mol ratios, were added and dissolved in distilled water for injection with stirring. Then, 0.3 g of sodium hydrosulfite was added as a stabilizer and the mixture was adjusted to pH about 7.4 with hydrochloric acid. The resulting aqueous nucleic acid component solution was filtered through a bacterial filter, filled into an infusion container and, after nitrogen purging, the container was closed tight and sterilized in an autoclave at 105° C. for 40 minutes to provide an anti-MRSA prophylactic/therapeutic composition according to the invention (total free nucleic acid component concentration 8 w/v%).

EXAMPLE 2

TABLE 2

| Nucleic acid component | w/v % | mMol/l | Mol ratio |
| --- | --- | --- | --- |
| 5'-CMP-2Na | 2.21 | 60.2 | 4 |
| 5'-GMP-2Na | 2.45 | 60.2 | 4 |
| 5'-UMP-2Na | 1.66 | 45.1 | 3 |
| 5'-IMP-2Na | 2.36 | 60.2 | 4 |
| Thymidine | 0.36 | 14.9 | 1 |
| Total free nucleic acid components | | 8 w/v % | |

Except that the above compounds were used as nucleic acid components, acetic acid was used for pH adjustment to about 7.3 and the autoclaving was performed at 110° C. for 40 minutes, the procedure of Example 1 was repeated to provide an anti-MRSA prophylactic/therapeutic composition of the invention (total free nucleic acid component concentration 8 w/v%).

EXAMPLE 3

TABLE 3

| Nucleic acid component | w/v % | mMol/l | Mol ratio |
| --- | --- | --- | --- |
| 5'-CMP-2Na | 1.12 | 30.5 | 2 |
| 5'-GMP-2Na | 1.24 | 30.5 | 2 |
| 5'-UMP-2Na | 0.56 | 15.2 | 1 |
| 5'-IMP-2Na | 1.20 | 30.6 | 2 |
| Thymidine | 0.37 | 15.3 | 1 |
| Total free nucleic acid components | | 4 w/v % | |

Except that the above compounds were used as nucleic acid components and the aqueous solution was adjusted to pH about 6.4, the procedure of Example 1 was repeated to provide an anti-MRSA prophylactic/therapeutic composition of the invention (total free nucleic acid components 4 w/v%).

EXAMPLE 4

TABLE 4

| Nucleic acid component | w/v % | mMol/l | Mol ratio |
| --- | --- | --- | --- |
| Cytidine | 0.73 | 30.0 | 4 |
| 5'-GMP-2Na | 1.22 | 30.0 | 4 |
| Uridine | 0.55 | 22.5 | 3 |
| Inosine | 0.80 | 29.8 | 4 |
| Thymidine | 0.18 | 7.4 | 1 |
| Total free nucleic acid components | | 3.4 w/v % | |

Except that the above compounds were used as nucleic acid components and no pH control agent was added, the procedure of Example 1 was repeated to provide an anti-MRSA prophylactic/therapeutic composition of the invention (total free nucleic acid components 3.4 w/v%).

EXAMPLE 5

As pure crystalline nucleic acid components, 2.7 g of inosine and 4.1 g of 5'-GMP-2Na were sieved through a 60-mesh screen, evenly blended and filled into a glass container to provide an anti-MRSA prophylactic/therapeutic composition of the invention in a powder form.

The mol ratio of inosine to 5'-GMP-2Na in this powder was about 1:1.

This powder can be extemporaneously dissolved in a suitable amount of purified water for parenteral administration.

TEST EXAMPLE 1

Protection test in MRSA-infected mice

Forty-nine female Balb/c mice, 4 weeks old, were put on a 20% casein diet for 30 days. Of these mice, 25 animals were assigned to a group to be treated with the anti-MRSA prophylactic/therapeutic composition (1) (the composition of Example 1) and the remaining 24 animals to a control group (1) given physiological saline. Beginning day 1 of feeding, 0.35 ml of the test composition or saline was intraperitoneally administered once a day and the body weights of mice were serially determined.

A similar experiment was carried out using 0.35 ml/dose/day of the anti-MRSA prophylactic/therapeutic composition (2) (the composition of Example 4) or the composition (3) (the composition shown below in Table 5) of the invention in lieu of the anti-MRSA prophylactic/therapeutic composition (1). Each test composition was administered to 25 mice. A control group (saline group (2)) of 25 mice was provided for the latter 2 experiments.

TABLE 5

| Nucleic acid component | w/v % | mmol/l | Mol ratio |
|---|---|---|---|
| Inosine | 0.80 | 29.8 | 4 |
| Cytidine | 0.007 | 0.3 | 0.04 |
| 5'-GMP-2Na | 1.22 | 30.0 | 4 |
| Uridine | 0.55 | 22.5 | 3 |
| Thymidine | 0.18 | 7.4 | 1 |
| Total free nucleic acid components | | 2.76 w/v % | |

As the tester *Staphylococus aureus*, a clinically isolated 8985N strain (confirmed to be methicillin-resistant) was subcultured on agar medium and, then, incubated in BHI broth at 37° C. for 18-24 hours. The culture was centrifuged (10000 rpm, 15 min.) and the cells were suspended in physiological saline to an absorbance of 1.0 at 660 nm. The viable cell count in the suspension, as determined by the method of Exlund and Lankford, was $2.1 \times 10^8$ CFU/ml.

On day 10 after the beginning of feeding, 0.3 ml of the above cell suspension was administered into the tail vein of each mouse. After this inoculation, the survival rate and the morbidity rate (associated with body weight loss etc.) were determined. In addition, all the surviving mice on day 20 after inoculation were sacrificed and the spleen, kidneys and heart were asetically isolated and respectively homogenized with physiological saline. The viable bacterial count in each homogenized organ sample was determined by the agar plate dilution method. The organ weights were also determined. As to the mice which had died by day 20 following inoculation, too, organ bacterial counts and weights were similarly determined.

As will be seen from the examples, the survival rate of control animals was 25% (6/24) in saline group 1 and 16% (4/25) in saline group 2 or, taken together, 20.4% (10/49). In contrast, the survival rate of treated mice was 72% (18/25) in composition (1) group, 80% (20/25) in composition (2) (composition of Example 4) group and 64% (16/25) in composition (3) (composition of Table 5) group. Thus, the survival rates in these groups treated with the compositions of the invention were significantly higher than the survival rates in the saline control groups (the survival rates on day 20 after inoculation were analyzed by $\chi^2$ test. $p < 0.01$). It is, therefore, clear that the pharmaceutical composition of the invention is effective in the prevention and therapy of MRSA infection.

Recovery from MRSA infection can be ascertained from the course of body weight regain. Thus, in both groups, surviving animals began to gain weight around day 10 after infection. On the other hand, in dead animals, body weigh loss after infection continued until they died in both groups.

Table 6 below shows the organ bacterial counts and weights (g) (spleen, kidneys and heart) of the mice which survived to day 20 after MRSA infection and those which died in the course in the group treated with the same composition (1) of the invention (invention group) and saline (control group), respectively.

TABLE 6

| | control group | | invention group | |
|---|---|---|---|---|
| | Deaths (n = 18) | Survivals (n = 6) | Deaths (n = 8) | Survivals (n = 17) |
| CFU ($\times 10^5$) in kidney | 3690 ± 1620 | 19 ± 27* | 2200 ± 1250 | 18 ± 31* |
| CFU ($\times 10^4$) in spleen | 17 ± 18 | 6 ± 10 | 24 ± 13 | 3 ± 1* |
| CFU ($\times 10^5$) in heart | 14 ± 31 | 2 ± 1 | 16 ± 22 | 4 ± 14 |
| Kidney weight (g) | 0.24 ± 0.03 | 0.21 ± 0.03 | 0.21 ± 0.01 | 0.23 ± 0.04 |
| Spleen weight (g) | 0.06 ± 0.01 | 0.21 ± 0.06* | 0.06 ± 0.01 | 0.13 ± 0.05* |
| Heart weight (g) | 0.09 ± 0.03 | 0.07 ± 0.01 | 0.08 ± 0.01 | 0.09 ± 0.02 |

*Significant difference ($p < 0.01$) from dead mice by Student's t-test

It is seen that whereas the viable count in the kidneys from dead mice was over $2.0 \times 10^8$ CFU in both of the invention and control groups, the count in the kidneys from surviving mice was less than $2.0 \times 10^6$ CFU in both groups. It is also clear that the viable counts in the heart and spleen are very low in both dead and surviving mice in both groups and that in regard to organ weights, the spleen weight is more than double in the surviving mice compared with dead mice in both groups. These results suggest the enhancement of immune response in survivals.

It is evident from the above findings that the anti-MRSA prophylactic/therapeutic composition of the invention significantly increases the resistance of individuals to MRSA infection.

Test Example 2

Therapeutic test in MRSA-infected mice

Sixty-nine female Balb/c mice, 4 weeks old, were put on a 20% casein diet for 30 days. On day 10 after the beginning of feeding, the animals were inoculated with MRSA in the same manner as described in Test Example 1. Beginning the day after inoculation, 0.35 ml of the anti-MRSA prophylactic/therapeutic composition (1)

(composition of Example 1) was intraperitoneally administered to 35 mice once a day (invention group). As a control, 0.35 ml of physiological saline was similarly administered to 34 mice (control group).

Table 7 shows the survival rate of mice in each group on day 20 after inoculation.

TABLE 7

| | Surviving mice (n) | Survival rate (%) |
|---|---|---|
| Composition (1) group (invention) | 24/35 | 68.6* |
| Saline group (control) | 10/34 | 29.4 |

*p<0.001 [Fisher's exact test].

It is apparent from Table 7 that the survival rate of mice in the invention group is significantly higher than that of mice in the control group, indicating the therapeutic efficacy of the anti-MRSA composition of the invention.

The above test was repeated except that each of the following anti-MRSA compositions [(2)–(9)] of the invention was used in lieu of the above composition (1).

(2) Composition of Example 4 (0.35 ml)

(3) Injectable composition of Table 5 as prepared in the same manner as Example 4 (0.35 ml)

(4) Inosine injection with 0.80 w/v% total free nucleic acid components as prepared in the same manner as Example 1 (inosine content 0.80 w/v%, 0.35 ml).

(5) Combination of 0.35 ml of the composition of Example 1 with 0.14 g of arginine (oral)

(6) Combination of 0.35 ml of the composition of Example 4 with 0.28 g of glutamine (oral)

(7) Combination of 0.35 ml of the composition of Example 4 with 0.14 g of arginine and 0.28 g of glutamine (oral)

(8) Combination of 0.35 ml of the above inosine injection (4) with 0.14 g of arginane and 0.28 g of glutamine (oral)

(9) Physiological saline (0.35 ml)

The results are shown below in Table 8.

TABLE 8

| Test drug | Surviving mice (n) | Survival rate (%) |
|---|---|---|
| (2) Composition of Example 4 | 14/17 | 82.4** |
| (3) Injection of Table 5 | 11/18 | 61.1* |
| (4) Inosine injection | 10/18 | 55.6* |
| (5) Composition of Example 1 + arginine | 13/17 | 76.5* |
| (6) Composition of Example 4 + glutamine | 13/17 | 76.5* |
| (7) Composition of Example 4 + arginine + glutamine | 15/17 | 88.2** |
| (8) Inosine injection + arginine + glutamine | 12/17 | 70.6* |
| (9) Physiological saline | 6/29 | 20.6 |

* and ** denote significant differences from saline group (9) at p<0.05 and p<0.01 [Fisher's exact test], respectively.

It is apparent from Table 8 that the anti-MRSA compositions of the invention show significant therapeutic effect to MRSA infection.

Test Example 3

Efficacy test of anti-MRSA oral nucleic acid

Eighty-four female Balb/c mice, 4 weeks old, were divided into 3 groups and 34 of them were put on a nucleic acid-free purified diet (NF, the following composition), 40 mice on a 0.5% RNA diet prepared by supplementing NF with 0.5% of RNA, and the remaining 10 mice on a 2.5% RNA diet (NF containing 2.5% RNA), all for 30 days.

| Formula of NF feed | Percent by weight |
|---|---|
| Corn starch | 41.5 |
| Casein | 25.0 |
| Alpha-starch | 10.0 |
| Cellulose powder | 8.0 |
| Linolic salad oil | 6.0 |
| AIN76 ™ Salt Mix (Oriental Yeast) | 3.5 |
| Granular sugar | 5.0 |
| AIN76 ™ Vitamin Mix (Oriental Yeast) + choline ditartarate | 1.0 |
| Total | 100.0 |

On day 10 after the beginning of feeding, mice in all groups were inoculated with MRSA in the same manner as in Test Example 2. Beginning the day after inoculation, 0.35 ml of physiological saline was intraperitoneally administered once a day to the mice on NF diet and those on 2.5% RNA diet. The 40 mice on 0.5% RNA diet were further divided into two groups of 20 animals and 0.35 ml of the anti-MRSA prophylactic/therapeutic composition of Example 1 of the invention was intraperitoneally administered once a day to one group (invention group), while 0.35 ml of physiological saline was similarly administered (saline group).

On day 20 after the inoculation, the survival rate of mice in each group was investigated. The results are shown in Table 9.

TABLE 9

| Group | Diet | Drug administered | Surviving animals (n) | Survival rate (%) |
|---|---|---|---|---|
| Control 1 | NF | Saline | 10/34 | 29.4 |
| Control 2 | 0.5% RNA | Saline | 7/20 | 35.0 |
| Control 3 | 2.5% RNA | Saline | 4/10 | 40.0 |
| Invention | 0.5% RNA | Composition of invention | 12/20 | 60.0* |

*significant difference from Control 1 at p<0.001 [Fisher's exact test]

It is apparent from Table 9 that whereas oral RNA does not contribute to resistance to MRSA infection, parenteral administration of the composition of the invention potentiates resistance to MRSA infection.

Test Example 4

Anti-MRSA protection test

Sixty-five female Balb/c mice, 4 weeks old, were put on a 20% casein diet for 30 days. The mice were divided into 6 groups of 10–12 individuals and beginning day 1 of feeding, each group of animals was dosed once daily with 0.80% (w/v%; the same applies hereinafter) inosine injection, 1.22% 5'-GMP-2Na injection, 0.73% cytidine injection, 0.55% uridine injection, 0.18% thymidine injection or physiological saline (control), all in 0.35 ml portions.

On day 10 after the beginning of feeding, the animals were inoculated with MRSA in the same manner as Test Example 1 and the survival rate of mice in each group was investigated on day 20 after inoculation. The results are shown in Table 10.

TABLE 10

| Group | Surviving animals (n) | Survival rate (%) |
|---|---|---|
| inosine injection group | 10/11 | 90.9* |
| 5'-GMP-2Na injection group | 8/10 | 80.0 |
| Cytidine injection group | 7/12 | 58.3 |
| Uridine injection group | 7/10 | 70.0 |
| Thymidine injection group | 8/11 | 72.7 |

TABLE 10-continued

| Group | Surviving animals (n) | Survival rate (%) |
|---|---|---|
| Physiological saline group | 4/11 | 36.4 |

*significant difference from saline control group at p<0.02 [Fisher's exact test]

It is apparent from Table 10 that compared with the survival rate of mice in the control group, the survival rates in the groups treated with the compositions of the invention (inosine injection, 5'-GMP-2Na injection, cytidine injection and thymidine injection groups) are invariably higher, with a significant difference in the inosine injection group, indicating a high anti-MRSA effect of the composition of the invention.

Test Example 5

Anti-MRSA protection test in mice on amino acid-enriched diet

One-hundred female Balb/c mice, 4 weeks old, were divided into 5 groups and one of these groups was put on a 20% casein diet. The second and third groups were put on the 20% casein diet supplemented with 2% of arginine and 4% of glutamine. In the third group, 0.35 ml of the anti-MRSA composition of Example 4 of the invention was administered intraperitoneally once daily. The fourth group of mice was put on the 20% casein diet supplemented with 2% of arginine and dosed intraperitoneally with 0.35 ml/dose/day of the anti-MRSA composition of Example 4 of the invention. The fifth group was put on the 20% casein diet supplemented with 4% of glutamine and dosed intraperitoneally with 0.35 ml/dose/day of the anti-MRSA composition of the invention.

On day 10 after the beginning of feeding, mice in each group were intravenously inoculated with MRSA in the same manner as Test Example 1. On day 8 after inoculation, the spleen was isolated and homogenized with sterile saline and the viable count in the homogenate was determined by the surface smear method using mannitol-agar medium. The anti-MRSA protection effect was evaluated with the viable count being regarded as the degree of elimination of bacteria in the mouse. The results are shown in Table 11.

TABLE 11

| Viable count | <10 | $10^4$–$10^5$ | $10^5$–$10^6$ | $10^6$–$10^7$ | $10^7$–$10^8$ |
|---|---|---|---|---|---|
| Group 1 | | | 20/20 | | |
| Group 2 | | 6/20 | 6/20 | 4/20 | 4/20 |
| Group 3 | 6/20 | 4/20 | 10/20 | | |
| Group 4 | 1/20 | 6/20 | 10/20 | 3/20 | |
| Group 5 | | 7/20 | 10/20 | 3/20 | |
| Group 1 vs. Group 2 | | | | $p<0.01$ | |
| Group 1 vs. Group 3 | | | | $p<0.01$ | |
| Group 1 vs. Group 4 | | | | $p<0.01$ | |
| Group 1 vs. Group 5 | | | | $p<0.01$ | |
| Group 2 vs. Group 3 | | | | $p<0.01$ | |
| Group 2 vs. Group 4 | | | | $p<0.01$ | |
| Group 3 vs. Group 4 | | | | $p<0.05$ | |
| Group 3 vs. Group 5 | | | | $p<0.05$ | |

As well be seen from Table 11, whereas the spleen viable count in Group 1 (control) was concentrated in the range of $10^5$–$10^6$ cells, the distribution was $10^4$–$10^8$ Group 2 (food supplemented with amino acid), $\leq 10^2$–$10^6$ in Group 3 (amino acid+composition of invention), $\leq 10^2$–$10^7$ in Group 4 (amino acid+composition of invention) and $10^4$–$17^7$ in Group 5 (amino acid+composition of invention). $\chi^2$test of the above data shows that compared with Group 1, the viable counts in Groups 2, 3, 4 and 5 are significantly low, that the viable counts in Groups 3 and 4 are significantly lower than the count in Group 2, and that the viable count in Group 3 is significantly lower than the counts in Groups 4 and 5.

Therefore, it is clear that the resistance to MRSA infection is increased when a standard diet is enriched with amino acid, i.e. arginine and/or glutamine, and that this enhancement of resistance to MRSA infection is further increased when this amino acid-enriched diet is used in combination with the anti-MRSA prophylactic/therapeutic composition of the invention. It is further clear that this effect is more pronounced with the combination of the composition of the invention with arginine and glutamine than with the combination of the composition with either arginine or glutamine.

What is claimed is:

1. A method of treating methicilin-resistant *Staphylococcus aureus* infections in a patient in need of such treatment which comprises administering to the patient an effective amount of a composition comprising at least one nucleic acid component selected from the group consisting of inosine, guanosine n'-monophosphate, uridine cytidine, adenosine n'-monophosphate, cytidine n'-monophosphate, uridine n'-monophosphate, inosine n'-monophosphate and thymidine.

2. A method according to claim 1, wherein the composition comprises inosine, cytidine, guanosine n'-monophosphate, uridine and thymidine in a mole ratio of 4:4:4:3:1.

3. A method according to claim 1, wherein the composition comprises adenosine n'-monophosphate, cytidine n'-monophosphate, guanosine n'-monophosphate, uridine n'-monophosphate and thymidine in a mole ratio of 4:4:4:3:1.

4. A method according to claim 1, wherein the composition comprises cytidine n'-monophosphate, guanosine n'-monophosphate, uridine n'-monophosphate, inosine n'-monophosphate and thymidine in a mole ratio of 4:4:3:4:1.

5. A method according to claim 1, wherein the composition comprises cytidine n'-monophosphate, guanosine n'-monophosphate, uridine n'-monophosphate, inosine n'-monophosphate and thymidine in a mole ratio of 2:2:1:2:1.

6. A method according to anyone of claims 1-5 wherein the composition further comprises at least one amino acid selected from the group consisting of arginine and glutamine.

* * * * *